United States Patent [19]

McCabe et al.

[11] Patent Number: 5,468,854
[45] Date of Patent: Nov. 21, 1995

[54] CHARACTERIZATION OF SPECIFIC DRUG RECEPTORS WITH FLUORESCENT LIGANDS

[75] Inventors: R. Tyler McCabe, Silver Spring; Brian R. de Costa, Rockville, both of Md.

[73] Assignee: Pharmaceutical Discovery Corporation, Elmsford, N.Y.

[21] Appl. No.: 95,937

[22] Filed: Jul. 22, 1993

Related U.S. Application Data

[63] Continuation of Ser. No. 739,183, Aug. 1, 1991, abandoned.
[51] Int. Cl.[6] ............... C07D 487/04; C07D 519/00
[52] U.S. Cl. ............... 540/498; 540/512; 548/125; 548/456; 548/463; 548/465; 548/466; 548/482; 549/223; 549/290; 549/394; 564/361; 564/428; 436/503
[58] Field of Search ........................ 540/498, 512

[56] References Cited

PUBLICATIONS

*The Merck Index*, 11th ed. (1989), Merck & Co., Inc., Rahway, N.J., pp. 401, 442, 646, 651, 1301.
R. Tyler McCabe, et al., Synapse:2:163–173 (1988).
R. Tyler McCabe, et al., *Pharmacology Biochemistry & Behavior*, vol. 37, pp. 365–370 (1990).
R. W. Olsen, et al., J. Chem. Neuroanatomy, vol. 3:59–76 (Jan. 1990).
R. H. Havunjian, et al., *J. Biol. Chem.* 265(36):22181–22186 (1990).
R. Tyler McCabe, et al., *Faseb J.* 4:2934–2940 (1990).
Correa, F. M. A., et al., *Neurosci. Lett.* 16, 47–53 (1990).
Atlas, D., and Levitzki, A., *Proc. Natl. Acad. Sci. USA* 74,5290–5294 (1977).
Henis, Y. I., et al. *Proc. Natl. Acad. Sci. USA* 79, 2907–2911 (1982).
Rademaker, B., et al., *Res. Commun. Chem. Pathol. Pharmacol.* 60, 147–159 (1988).
Kolb, V. M., et al., *Life Sci.* 33, 423–426 (1983).
Jacobson, K. A., *Biochem. Pharmacol.* 36, 1697–1707 (1987).
Heithier, H., et al., *Biochim. Biophys. Acta* 971, 298–306 (1988).
Ward, L. D., et al., *Biochim. Biophys. Acta* 971, 307–316 (1988).
Carlson, K. E., et al., *J. Steroid Biochem.* 32, 345–355 (1989).
Monsma, F. J., Jr., et al., *J. Neurochem.* 52, 1641–1644 (1989).
Velasquez, et al., *J. Neurosci.* 9:2163–2169 (1989).
Ariano, et al., *Proc. Natl. Acad. Sci. USA* 86:8570–8574 (1989).

*Primary Examiner*—Philip I. Datlow
*Attorney, Agent, or Firm*—Arnall Golden & Gregory

[57] ABSTRACT

Conjugates of fluorescent labels with specific, selective, and high affinity ligands for receptors have been synthesized and used to directly measure binding to receptors. In the examples, fluorescein conjugates of the high-affinity benzodiazepine receptor ligands Ro 15-1788 and Ro 7-1986 were synthesized. The binding of these fluorescent ligands (BD 621, BD 623 and BD 607) to benzodiazepine receptors was characterized by direct fluorescence measurement. Both the equilibrium dissociation constants ($K_D$) of BD 621 and BD 607 and the maximum number of binding sites ($B_{max}$) estimated by fluorescence monitoring were consistent with values obtained by using radioligand binding techniques. The binding of BD 621 and BD 607 assessed by fluorescence measurement was reversible, abolished by photoaffinity labeling with Ro 15-4513, and unaffected by a variety of substances that do not bind to benzodiazepine receptors. The potencies of chemically diverse benzodiazepine receptor compounds to inhibit fluorescent ligand binding were highly correlated, with potencies obtained from radioligand binding techniques. These findings demonstrate that direct fluorescence measurement techniques can be used to quantitate ligand-receptor interactions.

6 Claims, 2 Drawing Sheets

BD 621 (I)

BD 607 (II)

Ro 15-1788 (IV)

BD 623 (III)

Ro 15-1788 (IV)          BD 623 (III)

CHARACTERIZATION OF SPECIFIC DRUG RECEPTORS WITH FLUORESCENT LIGANDS

The United States has rights in this invention by virtue of NIH Grants NS22071, NS21908, HD06576 and HD22702. This is a continuation of application Ser. No. 07/739,183 filed on Aug. 1, 1991 now abandoned.

BACKGROUND OF THE INVENTION

This invention is generally in the area of methodologies for measuring binding reactions, specifically between drugs and drug receptors using fluorescent labels.

Radioligand binding techniques have been widely used for more than a decade to study receptor pharmacology and physiology. These methodologies provide a rapid, efficient means for drug discovery and identification of putative endogenous substances that may physiologically subserve receptors, as reviewed by Yamamura, H. I., Enna, S. J., and Kuhar, M. J., eds In *Neurotransmitter Receptor Binding*, 2nd ed. (Raven Press, New York 1988) and Snyder, S. H. "Drug and neurotransmitter receptors. New perspectives with clinical relevance." J. Am. Med. Assoc. 261, 3126–3129 (1989). These studies are particularly useful in characterizing drug-receptor interactions and specificities.

For example, in *J. Chem. Neuroanatomy*, 3:59–76 (January 1990), Olsen, R. W., R. T. McCabe, and J. K. Wamsley, described the characterization of $GABA_A$ receptor subtypes using autoradiographic comparison of GABA, benzodiazepine, and convulsant binding sites in the rat central nervous system. The regional distribution of radioactive ligand binding in rat brain for the different receptors of the gamma-aminobutyric $acid_A$ ($GABA_A$)-benzodiazepine receptor/chloride channel complex was measured on tissue sections by autoradiography. Seven ligands were employed including [$^3$H]muscimol for high-affinity GABA agonist sites; [$^3$H] bicuculline methochloride and [$^3$H]SR-95531 for the low-affinity GABA sites; [$^3$H]flunitrazepam for benzodiazepine sites, and [$^3$H]2-oxo-quazepam for the 'BZ1'-type subpopulation; and [$^{35}$S]t-butyl bicyclophosphorothionate (TBPS) and [$^3$H]t-butyl bicyclo-orthobenzoate (TBOB) for convulsant sites associated with the chloride channel. Allosteric interactions of benzodiazepine receptor ligands with [$^{35}$S] TBPS binding were also examined in membrane homogenates. Comparison of 19 brain regions indicated areas of overlap between these ligands, but also significant lack of correspondence in some regions between any two ligands compared. Significant differences were observed in comparing GABA agonists with antagonists, one antagonist with another, GABA ligands with benzodiazepine or convulsant sites, and even between the two convulsants TBPS and TBOB. It is likely that the characterization of receptors as subtypes based on binding alone indicate a pharmacological heterogeneity that might be exploited with subtype-specific drugs showing desirable clinical profiles.

As described by R. T. McCabe, D. R. Mahan, R. B. Smith, and J. K. Wamsley in *Pharmacology Biochem. Behavior* 37: 365–370 (May 1990), the binding of the triazolobenzodiazepine [$^3$H]alprazolam was studied to characterize the in vitro interactions with benzodiazepine receptors in membrane preparations of rat brain. Alprazolam, an agent used as an anxiolytic and in the treatment of depression, acts in vitro as a selective and specific ligand for benzodiazepine receptors in the rat brain. Studies using nonequilibrium and equilibrium binding conditions for [$^3$H]alprazolam resulted in high specific to nonspecific (signal to noise) binding ratios. The binding of [$^3$H]alprazolam was saturable and specific with a low nanomolar affinity for benzodiazepine receptors in the rat brain. GABA enhanced [$^3$H]alprazolam binding while several benzodiazepine receptor ligands were competitive inhibitors of this drug. Compounds that bound to other receptor sites had a very weak or negligible effect on [$^3$H]alprazolam binding.

Despite the usefulness and sensitivity of radioligand binding techniques, the use of alternative methods to study ligand-receptor interactions may provide information not readily accessible by conventional radioreceptor techniques and circumvent some of the drawbacks (such as high cost, disposal, and potential health hazard) associated with this methodology.

Fluorescence techniques have successfully been employed to study the behavior of ligand-protein interactions. For example, fluorescent labeled substrates and antigens have proven valuable in the examination of substrate-enzyme and antigen-antibody interactions.

Several attempts have been made to use fluorescent compounds to characterize receptors. Ligands with fluorescent moieties were prepared for α-adrenergic (Correa, F. M. A., et al., *Neurosci. Lett.* 16, 47–53 (1980)); β-adrenergic (Atlas, D., and Levitzki, A. *Proc. Natl. Acad. Sci. U.S.A.* 74, 5290–5294 (1977); Henis, Y. I., et al., *Proc. Natl. Acad. Sci. U.S.A.* 79, 2907–2911 (1982); and Rademaker, B., et al., *Res. Commun. Chem. Pathol. Pharmacol.* 60, 147–159 (1988)); opioid (Correa, et al., (1980) and Kolb, V. M., et al., *Life Sci.* 33, 423–426 (1983)); adenosine (Jacobson, K. A., et al., *Biochem. Pharmacol.* 36, 1697–1707 (1987)); glucagon (Heithier, H., et al., *Biochim. Biophys. Acta* 971, 298–306 (1988) and Ward, L. D., et al., *Biochim. Biophys. Acta* 971, 307–316 (1988)); steroid (Carlson, K. E., et al., *J. Steroid Biochem.* 32, 345–355 (1988)); and dopamine (Monsma, F. J., Jr., et al., *J. Neurochem.* 52, 1641–1644 (1989)) receptors.

Although many of the ligands with fluorescent moieties were reported to have moderate to high affinities when evaluated with radioligand assays, quantitation and visualization of ligand-receptor interactions by direct fluorescence measurement have been problematic. For example, investigations using fluorescent ligands to identify receptors were equivocal owing to high levels of tissue autofluorescence and apparent lack of specificity (Correa, F. M. A., et al., (1980), Rademaker, B., et al., (1988), (Hess, A. *Brain Res.* 160, 533–538 (1979); Barnes, P., et al., *Brain Res.* 181, 209–213 (1980); Rademaker, B., et al., *Eur. J. Pharmacol.* 111, 31–36 (1985); and Rademaker, B., et al., *J. Recept. Res.* 5, 121–131 (1985)). Carlson, et al. (1988) described an ethyl acetate extraction technique to analyze fluorescent ligands for steroid receptors. Nevertheless, direct quantitation of ligand-receptor interactions with fluorescent ligands has not been demonstrated conclusively.

It is therefore an object of the present invention to provide a method and reagents for use in directly quantitating ligand-receptor interactions with fluorescent ligands.

It is a further object of the present invention to provide a method and reagents for use in determining ligand-receptor interactions intracellularly and extracellularly.

SUMMARY OF THE INVENTION

Fluorescent labeled ligands were prepared for use in receptor binding studies by covalently binding a ligand, such as a compound specifically and selectively binding to benzodiazepine, opioid, N-methyl D-aspartate, β- and α-adrenergic, dopamine or serotonin receptors, to a fluorescent label, wherein the labeled ligand binds specifically to a receptor with an affinity of less than or equal to one micromolar and the label is directly detectable in the visible spectrum. The fluorescent labeled ligands are particularly useful in direct assays of binding intracellularly, as well as extracellularly, and in competitive binding studies to determine the specificity and affinity of uncharacterized compounds.

In the examples, fluorescein conjugates of the high-affinity benzodiazepine receptor ligands Ro 15-1788 and Ro 7-1986 were synthesized. The binding of these fluorescent ligands (BD 621, BD 623 and BD 607) to benzodiazepine receptors was characterized by direct fluorescence measurement. Both the equilibrium dissociation constants ($K_D$) of BD 621 and BD 607 and the maximum number of binding sites ($B_{max}$) estimated by fluorescence monitoring were consistent with values obtained by using radioligand binding techniques. The binding of BD 621 and BD 607 assessed by fluorescence measurement was reversible, abolished by photoaffinity labeling with Ro 15-4513, and unaffected by a variety of substances that do not bind to benzodiazepine receptors. BD 623 exhibited excitation and emission maxima at 486 and 542 nm, respectively, and possessed fluorescent properties that are dependent upon the polarity of its environment. BD 623 bound reversibly to benzodiazepine receptors in the central nervous system with an apparent affinity ($K_I$ 5.7 nM), comparable to the parent imidazobenzodiazepine 2.8 nM). Addition of BD 623 to a suspension of brain membranes resulted in a time-dependent quenching of its fluorescence. Fluorescence quenching of this compound was readily reversed by specific benzodiazepine receptor ligands but not by a variety of other substances. Moreover, inactivation of benzodiazepine receptors by photoaffinity labeling with Ro 15-4513 resulted in a reduction in the fluorescence quenching of BD 623 consistent with the reduction in density of benzodiazepine receptors measured using a radioreceptor assay. Monitoring of fluorescence/dequenching of BD 623 in real time permitted a quantitative characterization of the ligand-receptor interaction, with both the $K_d$ of BD 623 (13.9 nM) and $K_I$ of Ro 15-1788 (5.7 nM) comparable with the estimates obtained using radioreceptor techniques.

The potencies of chemically diverse benzodiazepine receptor compounds to inhibit fluorescent ligand binding were highly correlated with potencies obtained from radioligand binding techniques. These findings demonstrate that direct fluorescence measurement techniques can be used to quantitate ligand-receptor interactions. The results with BD 623 indicate that application of fluorescence quenching techniques are a useful adjunct for the study of specific receptors.

DETAILED DESCRIPTION OF THE INVENTION

It has now been discovered that it is possible to bind a fluorescent label to a specific ligand for receptors, especially receptors in the central nervous system (CNS), for use in quantitatively, sensitively and directly detecting binding of the ligand to the receptors, both in vitro in solution or suspension and intracellularly in cells or tissue. The process and reagents are particularly useful in targeting benzodiazepine, dopamine, opioid, N-methyl D-aspartate, β- and α-adrenergic, and serotonin receptors.

It is important that the fluorescent label be attached to the ligand at an appropriate site so as to not interfere with binding activity of the ligand nor with fluorescence of the label. It is also important to choose a label which emits detectable fluorescence at the desired wavelength(s), under the conditions under which it is to be detected, including pH, ionic strength, polarity of the solution (for example, water versus alcohol versus ethyl acetate), and amount and type of tissue present (for example, brain tissue versus kidney tissue versus lung tissue versus heart).

Advantages to the use of fluorescence include the rapidity with which results can be obtained (≤ milliseconds), allowing use of the label in following binding over time, in contrast to radioactivity, which requires reaching equilibrium (e.g., 60 minutes), then stopping of the reaction (15 to 60 seconds), then a relatively lengthy process (hours to days to months) to make a determination. Other advantages include the ability of some fluorescent labels to fluoresce at different wavelengths with different intensities under different conditions. The latter is useful in determining whether or not the labelled ligand has penetrated into a cell, since the conditions, for example, pH, intracellularly versus extracellularly are quite different. For example, one can also look at lateral mobility, the passage of molecules into and out of cells. This is not possible with radioactive labels. The intensity of some fluorescent labels also declines over time after binding, allowing one to measure binding kinetics with one label. One can also use a quenching ligand to reduce intensity, for example, where more than one fluorescent label has been used, to create a three dimensional structural/activity comparison of a receptor conformation.

The fluorescent labelled ligand can be used directly and quantitatively to measure and locate ligand-receptor interactions. Quantitation is achieved as described in more detail below, by measuring fluorescence at one or more specific wavelengths and comparing intensity with concentration on a standard line. Since the label is bound directly to the ligand which binds directly and specifically to the receptor, and tissue or cells do not have be removed prior to measurement, the assay is direct. This is in contrast to prior uses of fluorescent probes, such as Flura II™ (Molecular Probes, Eugene, Oreg.), which mimics calcium and has been used to measure flux into a cell. In this prior method, measurement requires that there be one or more intermediate steps to determine the presence of and effect on specific receptors.

FLUORESCENT LABELS

The criteria for selecting an appropriate fluorescent label are that it must not hinder binding by the ligand to the receptor, i.e, the specificity and selectivity of the ligand; and that it must be detectable in the visible spectrum.

Examples of suitable fluorescent labels include fluorescein, 5,6-carboxymethyl fluorescein, Texas red, nitrobenz-2-oxa-1,3-diazol-4-yl (NBD), coumarin, dansyl chloride, and rhodamine. The preferred label is fluorescein (5-carboxyfluorescein-N-hydroxysuccinimide ester) or rhodamine (5,6-tetramethyl rhodamine). These can be obtained from a variety of commercial sources, including Molecular Probes, Eugene, Oreg. and Research Organics, Cleveland, Ohio.

LIGANDS

The label is bound to a ligand known to bind to a receptor with high affinity (the likelihood of a ligand binding to a receptor, measured in terms of concentration), selectivity (rank order of potency of a ligand for a specific receptor as compared with others binding to the same receptor, measured in terms of concentration), and specificity (recognizing only one receptor, as compared to more than one receptor, for example, diazepin recognizes only benzodiazepine receptors and no other receptors, as compared to SCH 23390, which recognizes primarily dopamine type 1 receptors as well as serotonin receptors). Examples of preferred compounds for binding to CNS receptors include benzodiazepine and derivatives and related compounds thereof, dopamine, opioid, N-methyl D-aspartate (glycine or glutamate), β-adrenergic agonists and antagonists, α-adrenergic agonists and antagonists, and serotonin. As used herein, "ligand" includes bioactive compounds (drugs) or compounds known to bind to a particular receptor which may or may not exert a biological effect as a result of binding. There is no preferred size. The affinity should be less than one micromolar, preferably less than 100 nM.

PROCEDURES FOR BINDING LABEL TO LIGAND

Methods known to those skilled in the art are used to bind the label to the ligand. Examples are provided in detail below. In general, the label is bound to the ligand at a site where the label does not sterically hinder binding of the ligand to the receptor, usually through an amine group, using a protection-deprotection process. The site of attachment of the fluorescent label to the ligand is particularly important as compared with attachment of a radiolabel to the ligand since a radiolabel usually consists of one or two atoms while the fluorescent probe may be of the same size as the ligand and therefore much more likely to interfere with binding to the receptor. The label must also be bound so that the ligand does significantly interfere with or decrease the fluorescent intensity of the label.

In some cases, to avoid stearic interference, the label is bound to the ligand through a spacer. In the preferred embodiment, the spacer consists of a two to seven methylene carbon chain which prevents the label from interfering with the binding activity of the ligand.

METHODS FOR MEASURING FLUORESCENCE

The excitation and emission spectra of the fluorescent label are measured using commercially available instrumentation, for example, as described below. Quantitation of binding is accomplished by creating a standard line relating fluorescence intensity values (counts/s) to known amounts of fluorescent ligand in a tissue suspension or buffer. The amount of fluorescent ligand bound is estimated by linear regression using fluorescence intensity in tissue suspension versus ligand concentration (nM). The quantity of free ligand is directly assayed from fluorescence intensity measurements in buffer versus ligand concentration.

Displacement of fluorescent ligand binding to membranes or tissue is examined by incubating the ligands in the presence of varying concentrations of several competing compounds and quantitating fluorescence.

Analysis of intracellular events versus extracellular events is accomplished by choosing an appropriate fluorescent probe (e.g., fluorescein) which emits different fluorescent intensities depending on the pH of the environment, labeling the specific ligand with the label, and exposing the cells to the labelled ligand under conditions at which binding can occur. The pH of the inside of the cell is generally known (usually in the range of 7.4). The pH of the extracellular environment can be manipulated as desired to produce a difference in fluorescent intensity. For example, fluorescein has a low fluorescent intensity at pH 6.0 and optimum fluorescent intensity at pH 8.1. The fluorescein is ionized and the different intensities measured to quantitate the amount of intracellular versus extracellular binding.

The fluorescent labelled ligand can be used to screen compounds for specific binding to a receptor, either intracellularly or extracellularly, as described above, by competitive binding of the labelled ligand with the compound to be tested. Known concentrations of both labelled ligand and compound to be screened are added to the cells containing the receptor (or a solution, suspension or immobilized substrate containing receptor) under conditions at which binding should occur. The displacement of the labelled ligand is used to determine and quantitate the binding of the compound to be screened to the receptor.

The following examples demonstrate the use of a newly synthesized fluorescent ligand to study benzodiazepine receptors in a disrupted membrane preparation.

1,4-Benzodiazepines are commonly used in the treatment of a variety of disorders including insomnia, anxiety, and seizures. Several lines of evidence indicate these actions are mediated by specific receptors that are constituents of an oligomeric protein complex which regulates gamma-aminobutyric acid-gated chloride current through the neural membrane. Benzodiazepine receptors have been extensively studied because of the potential for discovery of novel pharmacological agents and their putative roles in pathophysiological processes ranging from anxiety to hepatic encephalopathy.

Figure 1:
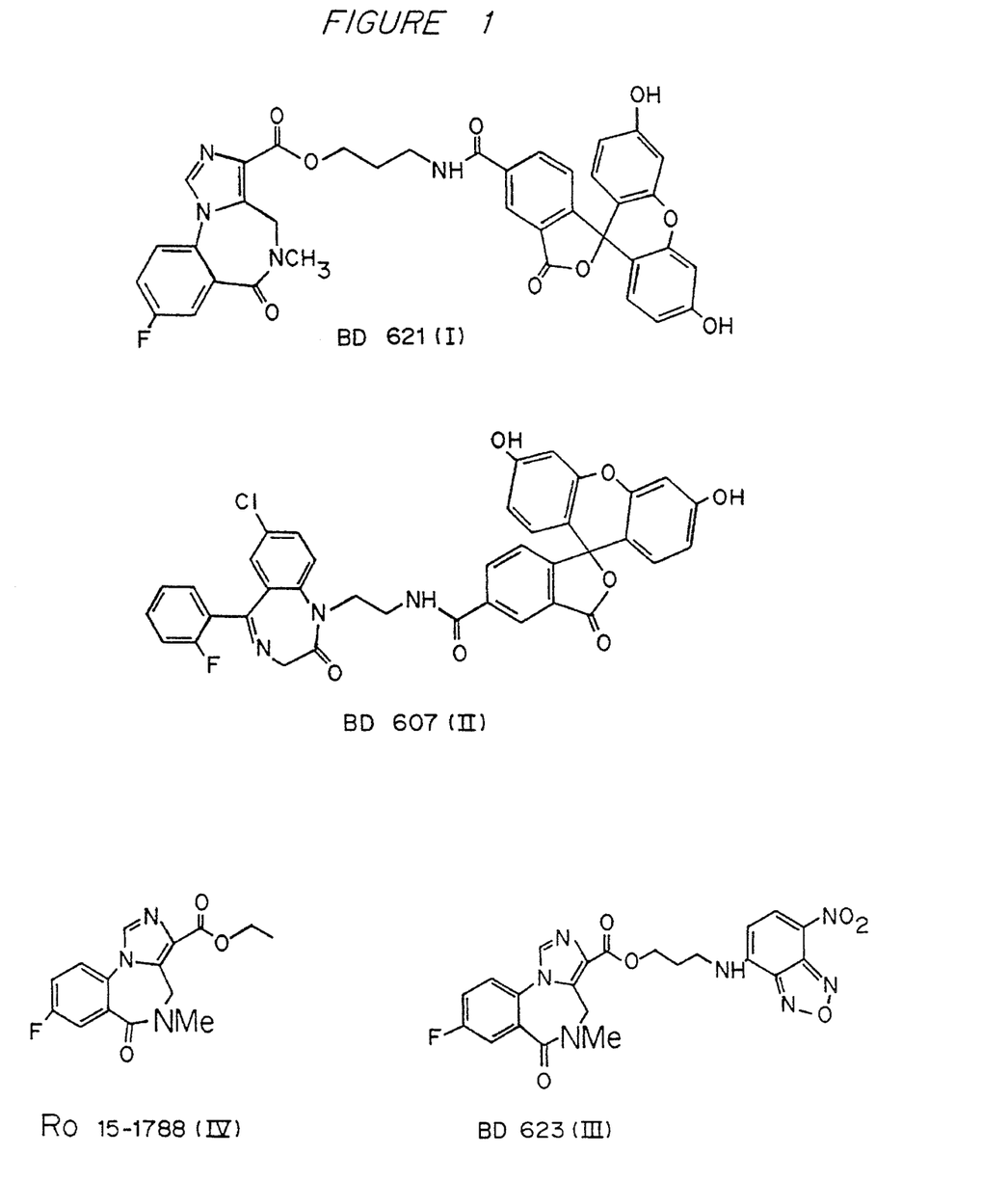
FIG. 1 illustrates the chemical structures of BD 621 (I), BD 607 (II), BD 623 (III), and the parent imidazobeazodiazepine Ro 15-1788 (IV), respectively.

Fluorescent conjugate of the imidazobenzodiazepine Ro 15-1788 were synthesized by attaching NBD to the parent ligand via an aminopropyl bridge (FIG. 1). The quantum yield of NBD is dependent upon the polarity of the environment (with the highest yield manifest in low polarity environments). The dependence of fluorescence intensity on the environment is shown by the significant enhancement of the fluorescent yield of BD-623 in the presence of membrane suspensions. NBD was selected as a suitable fluorophore since it is a relatively small apolar molecule that would not be expected to sterically hinder a ligand-receptor interaction if coupled to the parent molecule at an appropriate position using a suitable spacer group. NBD also has a relatively small dipole moment, reducing the possibility of an electrostatic interaction with the pharmacophore which would result in a loss in affinity compared to the parent compound.

The present invention will be further understood by the following non-limiting examples. The abbreviations used herein are: KOH, potassium hydroxide; DCC, N,N'-dicyclohexylcarbodiimide; H-NMR, proton nuclear magnetic resonance; IR, infra-red spectroscopy; DMF, N,N-dimethylformamide; BZ, benzodiazepine; CNS, central nervous systems; EIMS, electron ionization mass spectra; HRMS, high-resolution mass measurements; TLC, thin-layer chromatography; CIMS, chemical ionization mass spectra; NBD, 7-nitrobenz-2-oxa- 1,3-diazole. The teachings of the references cited in the following examples are specifically incorporated herein.

EXAMPLE 1

Synthesis of BD 621 (I) and BD 607 (II)

Synthesis of BD 621 (I) and BD 607 (II) commenced with Ro 15-1788 and Ro 7-1986, respectively. The chemical structures of BD 621 and BD 607 are shown in FIG. 1 (I) and (II). As described below, hydrolysis of Ro 15-1788 in 10% KOH/methanol afforded the corresponding carboxylic acid III in 97% yield. DCC-mediated coupling of III with 3-(N-t-butyloxycarbonyl)aminopropanol afforded IV in 40% yield. Quantitative N-deprotection of IV was effected with trifluoracetic acid at 4° C. to yield V, isolated as its trifluoroacetate salt. Although no attempt was made to further purify V because of its liability to ester-amide rearrangement, its base was sufficiently stable to allow $^1$H-NMR and IR characterization. Coupling of V with 5-carboxyfluorescein-N-hydroxysuccinimide ester in DMF in the presence of triethylamine afforded the target I in 44% yield. II was obtained in 62% yield by direct coupling of Ro 7-1986 with 5-carboxyfluorescein-N-hydroxysuccinimide ester in DMF.

Melting points were determined on a Thomas Hoover capillary apparatus and are uncorrected. CIMS were obtained using a Finnigan 1015 mass spectrometer. Californium-252 plasma desorption mass spectrometry (Cf-252 MS) was performed on a Cf- 252 plasma desorption mass spectrometer; samples were deposited on aluminized mylar film and spectra were acquired for 10 h at 15 kV. EIMS and HRMS were obtained using a V.G. Micro Mass 7070F mass spectrometer. $^1$H-NMR spectra were obtained using a Varian XL-300 spectrometer. IR spectra were determined using a Beckman 4230 IR spectrophotometer. Analytical TLC was performed on 250 μm Analtech GHLF silica gel plates.

5-Carboxyfluorescein-N-hydroxysuccinimide ester was purchased from Research Organics (Cleveland, Ohio). Ro 15-1788 and Ro 7-1986 were obtained as gifts from Hoffmann-La Roche (Nutley, N.J.).

8-Fluoro-5,6-dihydro-5-methyl-6-oxo-4H-imidazo[1,5-a] [1,4]benzodiazepine-3-carboxylic acid (III)

Ro 15-1788 (0.82 g, 2.71 mmol) was dissolved in 80 ml of 10% methanolic KOH and the solution was stirred for 24 h at room temperature. The solvent was evaporated in vacuo and the residue was dissolved in 50 ml of distilled water. The aqueous solution was cooled to 4° C. and the pH adjusted to 6 by dropwise addition of 1M aqueous HCl. The desired product was crystallized from the solution at pH 6. The solution was left to stand at 4° C. for 10 min and filtered. The filter cake was washed with ice-cold distilled water and dried overnight in vacuo at 60° C. to give III (0.72 g, 97%); crystallization from 50% aqueous ethanol (20 ml) afforded small colorless laminae: mp 273°–274° C.; $^1$H-NMR (d$_6$-DMSO) δ 3.08 (s, 3H, NMe), 4.60 (m, 1H), 5.05 (m, 1H), 7.60–7.67 (m, 2H), 7.79 (dd, 1H, J=4.5 Hz, J=8.50 Hz), 8.29 (s, 1H); IR (KBr) 2000–3600, 3110, 1700 (broad), 1670, 1490, 1220, 890 cm$^{-1}$; CIMS M+H=276, C$_{13}$H$_{10}$FN$_3$O$_{23}$ requires M+H=276. Analysis calculated for C$_{213}$H$_{10}$FN$_3$O$_3$:C 56.73, H 3.66, and N 15.27% showed C 56.80, H 3.71, and N 15.29%.

8-Fluoro-5,6-dihydro-5-methyl-6-oxo-4H-imidazo[1,5a] [1,4]benzodiazepine-3-carboxylic acid, 2-[[( 1,1-dimethylethoxy)carbonyl]-amino]propyl ester (IV)

DCC (0.44 g, 2.17 mmol) was added to a stirred solution of III (0.30 g, 1.09 mmol), 4-(N,N-dimethylamino)pyridine (0.13 g, 1.09 mmol), and 3-(N-t-butyloxycarbonyl)aminopropanol (0.38 g, 2.17 mmol) in dry methylene chloride (5 ml) and the solution was stirred overnight at room temperature. The reaction mixture was filtered and the filter cake washed with 10 ml of ether. The combined filtrate and washings were evaporated in vacuo, and the residue was fractionated by column chromatography on silica gel, eluting with concentrated aqueous ammonia-methanol-chloroform (1:9:90). Fractions corresponding to the major product were evaporated in vacuo to give IV (0.19 g, 40%) as a colorless oil: $^1$H-NMR (CDCl$_3$) 1.44 (s, 9H, t-Bu), 2.02 (t, J=6.3 Hz, 2H), 3.25 (s, 3H, NMe), 3.29 (m, 2H), 3.66 (t, 2H, J=5.7 Hz), 4.40 (m, 1H), 4.44 (t, 2H, J=6.1 Hz), 4.60–5.00 (m, 1H, NH), 5.22 (m, 1H), 7.32–7.45 (m, 2H), 7.78 (dd, 1H, J=2.8 Hz, J=8.7 Hz), 7.86 (s, 1H); HRMS m/z calculated for C$_{21}$H$_{25}$N$_4$O$_5$F 432.1807, m/z found 432.1796.

8-Fluoro-5,6-dihydro-5-methyl-6-oxo-4H-imidazo[1,5-a] [1,4]benzodiazepine-3-carboxylic acid, 3-aminopropyl ester (V)

Trifluoroacetic acid (1.0 ml) was added to a stirred solution (4° C.) of IV (0.19 g, 0.44 mmol) in dry chloroform (5 ml), and stirring continued for 1 h. The solvent was evaporated in vacuo and the oily residue subjected to high vacuum to give the trifluoroacetate salt of V (quantitative) as a colorless oil. No attempt was made to convert this salt to the free base or to further purify it because of its liability to rearrangement of the 3-aminopropyl ester side chain. However, for purposes of characterization, a small portion of the salt was converted to the free base by partitioning between chloroform and saturated NaHCO$_3$-V free base exhibited $^1$H-NMR δ 1.97 (m, 4H), 2.91 (m, 2H), 3.25 (s, 3H), 4.41 (m, 1H), 4.48 (br s, 2H, NH$_2$), 5.20 (m, 1H), 7.32–7.47 (m, 2H), 7.78 (dd, 1H, J=2.8 Hz, J= 8.7 Hz), 7.89 (s, 1H); IR (CHlCl$_3$) 3680, 3400, 3010, 1705, 1645, 1585, 1500, 1280, 1230, 1180, 1060 cm$^{-1}$; HRMS m/z calculated for C$_{16}$H$_{17}$FN$_4$O$_3$ 332.1277, m/z found 332.1284.

8-Fluoro-5,6-dihydro-5-methyl-6-oxo-4H-imidazo[1.5a] [1,4]benzodiazepine-3-carboxylic acid, 3-[[[1,3-dihydro-1,1-bis(4-hydroxypenyl)-3-oxo-5-isobenzofuranyl] carbonyl]amino]propyl ester (I)

A stirred solution of trifluoroacetate salt of V (28.2 mg, 0,058 mmol) and 5-carboxyfluorescein-N-hydroxysuccinimide ester (27.2 mg, 0.057 mmol) in dry DMF (3.0 ml) was treated with triethylamine (80 μl, 0.57 mmol), and the reaction mixture was stirred overnight at room temperature. The solvent was evaporated in vacuo, and the residue was applied to one 20 cm× 20 cm×1 mm preparative thin-layer chromatography plate, eluting with concentrated aqueous ammonia-methanol-chloroform (1:9:15). The band corresponding to the product was removed and extracted with the same solvent system (30 ml). Filtration and evaporation of the solvent afforded 17.2 mg (44%) of BD 621 as a pale yellow amorphous solid that was homogeneous by TLC: $^1\delta$ H-NMR 2.95 (m, 4H), 2.95 (m, 2H), 4.80 (br s, 1H, NH), 5.00 (m, 1H), 5.45 (m, 1H), 7.01 (d, 4H, d, J=5.7 Hz), 7.13–8.92 (m, 11H, ArH), 9.38 (br s, 1H, ArOH) Cf-252 MS M+H=691, M+Na=713, and M+ 2Na-H=735. $C_{37}H_{27}FN_4O_9$ requires M+H=691.

N-[2-[7-Chloro-5-(2-fluorophenyl)-2,3-dihydro-2-oxo-1H-1,4-benzodiazepin-1-yl]ethyl]-1,3-dihydro-1,1-bis(4-hydroxyphenyl)-3-oxo-5-isobenzofurancarboxamide (II)

5-Carboxyfluorescein-N-hydroxysuccinimide ester (20.6 mg, 0.044 mmol) was added to a stirred solution of Ro 7-1986 (38.5 mg, 0.116 mmol) in dry DMF (1 ml) and the solution was stirred overnight at room temperature. The DMF was removed under high vacuum at 60° C. and the residue was applied to one 20 cm×20 cm×1 mm preparative thin-layer chromatography plate, eluting with concentrated aqueous ammonia-methanol-chloroform (3.5:31.5:65). The band corresponding to the product was removed and extracted with 50 ml concentrated aqueous ammonia-methanolchloroform (5:45:50). Filtration and evaporation of the solvent afforded II (18.6 mg, 62%) as an amorphous yellow solid that was purified by TLC: $^1$H-NMR $\delta$ 1.14 (s, 1H), 2.49 (t, J=1.75 Hz, 2H), 3.83 (d, J=10.8 Hz, 2H), 3.96 (m, 1H), 4.35 (m, 1H), 4.64 (d, J=10.8 Hz, 2H), 6.53 (bs, 4H), 6.67 (s, 2H), 7.12–7.80 (m, 7H) 8.16 (m, 1H), 8.37 (s, 1H), 8.92 (m, 1H); Cf-252 MS M+H= 690, M+Na=712, M+2Na-H= 734. $C_{38}H_{25}[^{35}Cl]FN_3O_7$ requires M+H= 690.

EXAMPLE 2

Demonstration of Binding of BD 621 (I) and BD 607 (II) and Comparison with Radioligand Binding

TISSUE PREPARATION

Male Sprague-Dawley rats (Taconic Farms, Germantown, N.Y.) weighing 150–200 g were housed under a 12-h light/dark cycle (lights on 0700) with free access to food and water. Animals anesthetized with $CO_3$ were killed by decapitation. Brains were immediately excised and placed in ice-cold 50 mM Tris-citrate buffer (pH 7.4). Cerebral cortices were dissected and homogenized with a Brinkmann Polytron (setting 6–7, 15 s) in 20 vol of ice-cold buffer. Disrupted tissues were centrifuged at 23,000×g for 20 min at 4° C. Pellets were resuspended in an equal volume of buffer and recentrifuged. This procedure was performed four times. The tissue pellets were frozen over $CO_2$ and stores at −80° C. for 1–3 days before assay. The pellets were resuspended in 10–150 vol of buffer before assay. Protein was determined by using the Pierce (Rockford, Ill.) BCA Protein Assay Reagent.

FLUORESCENT LIGAND BINDING

Fluorescence intensity was measured with a SPEX Fluorolog Model 1680 0.22-m Double Spectrometer with DM3000 software (SPEX Industries, Edison, N.J.). The excitation and emission spectra were determined for fluorescent compounds and routinely used for analysis of ligand binding assays. BD 621 (1 µM) or BD 607 (1 µM) were placed in buffer (50 mM Tris-citrate, pH 7.4 at 4° C.) or tissue suspension equivalent to that used in binding experiments. The excitation maximum for BD 621 was 499 nm and the emission maximum was 529 nm. BD 607 yielded excitation and emission maxima of 494 and 521 nm, respectively. These values were not altered in a consistent manner by buffer composition or temperature.

Association studies were performed by incubating (4° C.) cortical membranes in polypropylene tubes containing buffer and fluorescent ligand for 1–70 min. The 1-ml incubation volume consisted of 980 µl tissue homogenate (routinely 300 µg protein/assay), 10 µl fluorescent ligand (50 nM and 10 µM) or buffer. Incubations were terminated by centrifugation for 10 min at 20,000×g (4° C.) in a Hermle Z360K centrifuge (Berthold Hermle GmgH & Co., Gosheim, FGR). The pellets were washed with 2× 300-µl aliquots of ice-cold buffer and resuspended by sonication in the original buffer volume. Samples were transferred to polystyrene cuvettes (Sarstedt, Newton, N.C.) and the fluorescence intensity measured. Nonspecific binding was determined in the presence of 10 µM diazepam. Reversibility experiments were accomplished by incubating tissues with fluorescent ligands (50 nM) for 1 h before adding diazepam (10 µM) to initiate dissociation. The reactions were terminated by centrifugation (20,000×g at 4° C. for 10 min) at 1-s to 30-min intervals. Optimum tissue concentration for binding was assessed by incubating fluorescent ligands (250 nM) with variable tissue amounts (20–300 µg protein/assay).

Saturation isotherms were constructed by incubating cortical membranes at 60° C. for 60 min with varying concentrations (8–1024 nM) of BD 621 or BD 607. The assay conditions used were identical to those described above.

Quantitation of BD 621 and BD 607 binding was accomplished by creating a standard line relating fluorescence intensity values (counts/s) to known amounts (1–1024 nM) of fluorescent ligand in tissue suspension or buffer. The amount of fluorescent ligand bound was estimated by linear regression using fluorescence intensity in tissue suspension vs. ligand concentration (nM). The quantity of free ligand was directly assessed from fluorescence intensity measurements in buffer vs. ligand concentration. The fluorescence intensity of BD 621 and BD 607 in tissue suspension was higher than in buffer, and higher than the sum predicted by fluorescence intensity of ligand in buffer plus the native tissue fluorescence. Standardization was performed daily to minimize experimental variability.

Photoaffinity labeling of BZ receptors was performed by pre-incubating membrane suspensions for 1 h in the presence or absence of 1 µM Ro 15-4513, using the method Sieghart, W., *J. Neurochem.* 48, 46–52 (1985). Tissues were then irradiated with UV light (366 nm) for 15 min and centrifuged (20,000×g for 10 min at 4° C.). The tissue pellets were washed in approximately 100 vol of buffer and recentrifuged. This washing procedure was repeated three times. BD 621 and BD 607 (50 nM) binding to photoaffinity labeled membranes was performed as described above. Diazepam (10 µM) defined nonspecific binding.

Displacement of 50 nM BD 621 or BD 607 binding to membranes was examined by incubating these ligands in the presence of varying concentrations of several compounds. Incubations and fluorescence measurements were performed as described above. The following substances were investigated: Ro 15-1788 (0.25–16 nM), triazolam (0.25–32 nM), diazepam (4–128 nM), flurazepam (2–128 nM), ethyl-β-carboline-3-carboxylate (β-CCE: 0.5–32 nM), and CL 218, 872 (16–1024 nM). Additional agents tested include: atropine (64–2048 nM), naloxone (64–2048 nM), propranolol (64–2048 nM), serotonin (64–2048 nM), Ro 5-4864 (64–2048 nM), and bicuculline methiodide (BMI: 64–2048 nM).

For determining standardization and quantitation of fluorescent ligand binding, measured as fluorescence intensity (cps) versus BD 621 concentration in nM, increasing concentrations (1–1024 nM; 2–64 nM) of fluorescent ligand were added to cuvettes containing cortical tissue suspension (approximately 300 µg protein/assay) or buffer (50 mM Tris-citrate, pH 7.4 at 4° C.). The standard line of increasing concentrations of BD 621 in tissue suspension vs. fluorescence intensity had a slope=889 and r=0.999. This line was routinely used to quantitate fluorescent ligand bound to BZ receptors. The standard line of increasing concentrations of BD 621 in buffer having a slope=482 and r=0.998 was used for estimation of free ligand. Standard lines were constructed with each experiment. Intensity of the tissue suspension without fluorescent ligand was 982±9 cps, and the intensity of buffer (without fluorescent ligand) was 258±13 cps. Fluorescence intensity of BD 621 in tissue suspension was greater than the predicted sum of the intensity of fluorescent ligand in buffer plus tissue autofluorescence. This increased intensity was not time dependent and remained unaffected by excess diazepam (10 µM), which indicates an altered solvent environment rather than a ligand-receptor binding effect. In support of this theory, fluorescence intensities of BD 621 and BD 607 were greatly increased in ethyl acetate and reduced in ethanol compared with intensities found in tissue suspension or buffer. This also demonstrates how one can use altered environment to localize the labeled ligand.

RADIOLIGAND BINDING

Assays were performed in a total volume of 500 µl consisting of: 400 µl membrane suspension (approximately 300 µg protein/assay) in 50 mM Tris-citrate buffer (pH 7.4 at 4° C.), 50 µl radioligand solution ([$^3$H]Ro 15-1788, sp act 78.0 Ci/mmol or [$^3$H]flunitrazepam, sp act 90.0 Ci/mmol), and 50 µl of drug or buffer. Diazepam (10 µM) was used to define nonspecific binding.

Reactions were initiated by adding the tissue homogenate and terminated 1 h later by centrifugation for 10 min at 20,000×g (4° C.). The supernatant was aspirated and the pellet rinsed superficially with 2×300-µl aliquots of buffer (4° C.), solubilized in 100 µl NCS (hersham, Arlington Heights, Ill.) at room temperature for 30 min, and neutralized with glacial acetic acid (10 µl). In some experiments, completed incubations were rapidly filtered through Whatman GF/B filters using a Brandel M-48 R (Gaithersburg, Md.) cell harvester, followed by two 5-ml washes with ice-cold buffer. Radioactivity was monitored in a Beckman LS 5801 liquid scintillation counter.

Saturation binding isotherms were constructed by incubating (4° C.) cortical membrane suspensions with 0.25–12 nM radioligand ([$^3$H]Ro 15-1788 or [$^3$H] flunitrazepam). Ro 15-4513 (1 µM) was used to photoaffinity label BZ receptors as described by Sieghart, et al., (1985). The binding of [$^3$H] Ro 15-1788 (1.6 nM) and fluorescent ligands (50 nM) to photoaffinity labeled tissues was compared. Inhibition of [$^3$H] Ro 15-1788 (0.7 nM) binding by BD 621 (8-1024 nM), BD 607 (8-1024 nM), Ro 15-1788 (0.25–16 nM), triazolam (0.25–32 nM), diazepam (4–128 nM), flurazepam (2–128 nM), β-CCE (0.5–32 nM), and CL 218,872 (16– 1024 nM) was performed to assess the potencies of these compounds for BZ receptors. Displacement by variable concentrations (64– 2048 nM) of atropine, naloxone, propranolol, serotonin, Ro 5-4864, and BMI was also examined. All assays were terminated by centrifugation unless otherwise specified.

LIGAND BINDING

For association of BD 621 binding to cortical membranes, tissues were incubated (4° C.) for 1–70 min in buffer containing 50 nM BD 621. Incubations were terminated by centrifugation at 20,000×g for 10 min at 4° C. Under these conditions, equilibrium was attained by 20 min. A 1-h incubation period was routinely used in other experiments. $LR_e$ is the concentration of ligand bound at equilibrium, and LR is the concentration of ligand bound at each time interval. The $k_{obs}$ and $k_1$ estimates for BD 621 were 0.250 min" and $3.08 \times 10^6 M^{-1}$ min$^{-1}$, respectively. For dissociation of fluorescent ligand binding, graphs were constructed by plotting ln (LR/$LR_o$) vs. time, where $LR_o$ represents the concentration of ligand-receptor complex before initiating dissociation. The dissociation rate constant ($k_{-1}$) was 0.096 min$^{-1}$. The $K_o$ estimated by nonequilibrium methods was 31 nM. Saturation isotherm for BD 621 binding to cortical membranes was determined for ligand concentrations varying from 8 to 1024 nM. Nonspecific binding was defined by 10 µM diazepam. A representative plot yielded $K_o$ and $B_{max}$ values of 54.6 nM and 2.9 pmol/mg protein, respectively. A Scatchard plot was calculated from the BD 621 saturation data. Data for corresponding saturation experiments with BD 607 are shown in Table 1.

The binding of BD 621 and BD 607 (8–1024 nM) to cortical membranes was saturable. Equilibrium binding results for BD 621, BD 607, [$^3$H] Ro 15-1788, and [$^3$H] flunitrazepam are summarized in Table 1. The $K_D$ value for BD 621 (63±3 nM) was consistent with the values from nonequilibrium studies. The $B_{max}$ estimates using BD 621 and BD 607 (3.6±0.5 and 4.5±0.2 pmol/mg protein, respectively) were not significantly different from values obtained using [$^3$H] Ro 15-1788 and [$^3$H] flunitrazepam (3.6±0.2 and 4.1±0.1 pmol/mg protein, respectively). Photoaffinity labeling tissues with Ro 15-4513 (1 µM) significantly reduced the specific binding of BD 621 (50 nM) and [$^3$H] Ro 15-1788 (1.6 nM) to an equivalent extent (Table 2).

Curves illustrating the inhibition of BD 621 (50 nM) binding by Ro 15-1788, triazolam, diazepam, and CL 218, 872 are shown by inhibition of BD 621 (50 nM) binding by Ro 15-1788 (0.25–16 nM), triazolam (0.25–32 nM), diazepam (4–128 nM), and CL 218,872 (16–1024 nM). Plots demonstrate mass action displacement of BD 621 binding to BZ receptors. The $K_I$ values were: Ro 15- 1788 (0.7±0.1 nM), triazolam (1.1±0.3 nM), diazepam (18±1.9 nM), CL 218,872 (90±25 nM), β-CCE (6.4±0.2 nM), and flurazepam (23±2.9 nM). $K_I$ values for inhibition of BD 607 (50 nM) binding were: Ro 15-1788 (6.6±1.2 nM), triazolam (0.7±0.2 nM), β-CCE (8.9±1.9 nM), diazepam (11.4±6.5 nM), flurazepam (34.2±3.4 nM), and CL 218,872 (115±40 nM). No significant reduction in BD 621 or BD 607 binding was observed using 64–2048 nM atropine, naloxone, propranolol, serotonin, Ro 5-4864, or BMI. Inhibition of [$^3$H] Ro 15-1788 (0.7 nM) binding to cortical membranes (reactions terminated by centrifugation) by BZ receptor ligands yielded the following $K_I$ values: triazolam (1.6±0.1 nM), Ro 15-1788 (2.5±0.1 nM), β-CCE (12±3.0 nM), diazepam (26± 2.0 nM), flurazepam (41±1.0 nM), and CL 218,872 (205±3.5). [$^3$H] Ro 15-1788 binding was not altered by 64–2048 nM atropine, naloxone, propranolol, serotonin, Ro 5-4864, or BMI. Displacement of [$^3$H] Ro 15-1788 (0.7 nM)

binding by BD 621 and BD 607 elicited the following inhibitory constants ($K_i$): 208±26 and 165±3 nM, respectively.

The relationship between the potencies of BZ receptor ligands as inhibitors of fluorescent ligand and radioligand binding were determined. $K_i$ (nM) values were assessed in competition with BD 621 and BD 607 by relating $K_i$ values plotted on the ordinate against [$^3$H] Ro 15-1788 binding plotted on the abscissa. Experiments were performed using cortical membranes. Data (means ±SEM) are from displacement studies and the plots of specific binding versus concentration of inhibitor. Inhibitors used were: Ro 1501788, triazolam, β-CCE, diazepam, flurazepam, and CL 218,872 (used for calculating the correlation coefficient). The correlation coefficient of fluorescent ligand binding vs. radioligand binding was r=0.94 (P<0.001).

The potencies of BZ receptor ligands to inhibit BD 621 and BD 607 binding to cortical membranes were highly correlated (r=0.94, P<0.001) with their potencies to displace [$^3$H] Ro 15- 1788 binding. The $K_i$ estimates for inhibition of BD 621 and [$^3$H] Ro 15-1788 binding in cerebellar membrane were, respectively: Ro 15-1788 (0.8±0.3 nM, 3.2±0.5 nM), β-CCE (3.7±2.5 nM, 10± 0.3 nM), flurazepam (14±1.4 nM, 51±0.2 nM), and CL 218,872 (62±7.7 nM, 239±19 nM).

TABLE 1

Equilibrium binding properties of BD 621 and BD 607 binding to BZ receptors: comparison with [$^3$H] flunitrazepam binding[a]

| Compound | $B_{max}$ | $K_D$ |
| --- | --- | --- |
| BD 621 | 3.6 ± 0.5 | 63 ± 3 |
| BD 607 | 4.5 ± 0.2 | 74 ± 4 |
| [$^3$H] Ro 15-1788 | 3.6 ± 0.2 | 3.4 ± 0.2 |
| [$^3$H] flunitrazepam | 4.1 ± 0.1 | 3.4 ± 0.5 |

[a]Saturation isotherms were constructed from data obtained by incubating (4° C.) cortical membranes with BD 621 (8-1024 nM), BD 607 (8-1024 nM), [$^3$H] Ro 15-1788 (0.25-12 nM), or [$^3$H] flunitrazepam (0.25-12 nM). Binding reactions were terminated by centrifugation as specified in Methods. $K_D$ (nM) and $B_{max}$ (pmol/mg protein) values for each ligand were determined from saturation isotherms using Graphpad (ISI Software, Philadelphia, Pa.) The $B_{max}$ values did not differ significantly among the four drug groups (ANOVA: F test = 1.767, P = 0.21). Alternatively, filtration was used to terminate additional saturation reactions and yielded the following $K_D$ and $B_{max}$ estimates: 3.3 ± 0.1 nM and 2.3 ± 0.2 pmol/mg protein for [$^3$H] Ro 15-1788; 2.6 ± 0.1 nM and 2.5 ± 0.3 pmol/mg protein for [$^3$H] flunitrazepam. $B_{max}$ estimates obtained using centrifugation were significantly different compared with values from filtration methods (ANOVA: F test = 7.605, P = 0.0008). Values are means ± SEM from three separate determinations.

TABLE 2

Attenuation of fluorescent ligand and radioligand and radioligand binding to BZ receptors in tissues photoaffinity labeled with Ro 15-4513[a]

| Drug | Control | UV + Ro 15-4513 |
| --- | --- | --- |
| BD 621, pmol/assay | 2.3 ± 0.2 | 0.08 ± 0.01[b] (−97%) |
| [$^3$H] Ro 15-1788, fmol/assay | 242 ± 9 | 14 ± 1.0[b] (−96%) |

[a]Experiments were performed as described in Methods. Membrane suspensions were preincubated (4° C.) for 1 h in the absence (control) or presence of Ro 15-4513 (1 µM). Both groups were subsequently irradiated with UV light (366 nm) for 15 min. Samples were then centrifuged (20,000 × g for 10 min, 4° C.) and extensively washed before assay with BD 621 (50 nM) or [$^3$H] Ro 15-1788 (1.6 nM). Values are means ± SEM of two independent determinations, each performed in triplicate. Student's t test (two-tailed).
[b]P < 0.01 compared with control.

The $K_D$ values of BD 621 and BD 607 binding to cortical membranes determined by fluorescence measurement and $K_i$ values estimated by inhibition of radioligand binding demonstrate that their apparent affinities for BZ receptors are reduced compared with those of the parent BZs Ro 15-1788 and Ro 7-1986. Both the introduction of a bulky fluorescein molecule and the presence of additional loci for hydrogen bonding may account for the decreased affinities of BD 621 and BD 607. However, the apparent affinities for BD 621 and BD 607 were high enough to permit separation of bound from free ligands using centrifugation, as the $B_{max}$ values obtained by fluorescence measurement were similar to those derived by radioligand binding.

These results demonstrate that ligand-receptor interactions can be quantitatively characterized by direct fluorescence measurement.

EXAMPLE 3

Synthesis of BD-623, a fluorescent quenching derivative of imidazobenzodiazepine.

MATERIALS 1,4-Benzodiazepines were obtained from Hoffmann-LaRoche, Nutley, N.J. CGS 8216 and buspirone were obtained from Ciba-Geigy (Summit, N.J.) and Bristol-Myers (Wallingford, Conn.), respectively. Naloxone HCl was synthesized at the National Institutes of Health. Phenteramine was purchased from Sigma. [$^3$H] Ro 15-1788 (specific activity 82.8 Ci/mmol) was purchased from DuPont-New England Nuclear (Boston, Mass.). 4-Fluoro-7-nitrobenz-2-oxa-1,3-diazole (NBD-fluoride) was purchased from Molecular Probes, Eugene, Oreg. All other materials were obtained from conventional sources.

Methods of analysis were as described in example 1.

8-Fluoro-5,6-dihydro-5-methyl-6-oxo-4H-imidazo[1,5a] 1,4]benzodiazepine-3-carboxylic Acid (1)

Ro 15-1788 (0.82 g, 2.71 mmol) was dissolved in 80 ml of 10% methanolic KOH, and the solution was stirred for 24 h at room temperature. The solvent was evaporated in vacuo, and the residue was dissolved in 50 ml of distilled water. The aqueous solution was cooled to 4° C., and the pH was adjusted to 6 by dropwise addition of 1 m HCl. The desired product crystallized from solution at pH 6. The solution was left to stand at 4° C. for 10 min and filtered. The filter cake was washed with cold (4° C.) distilled water and dried overnight in vacuo at 60° C. to give (1) (0.72 g, 97%); crystallization from 50% aqueous ethanol (20 ml) afforded small colorless laminae: m.p. 273°–274 ° C.; $^1$H NMR (d$_6$Me$_2$SO) δ 3.08 (s, 3H, NMe), 4.60 (m, 1H), 5.05 (m, 1H), 7.6014 7.67 (m, 2H), 7.79 (dd, 1H, J=4.5 Hz, J=8.50 Hz), 8.29 (s, 1H); IR (KBr) 2000– 3600, 3110, 1700 (broad), 1670, 1490, 1220, 890 cm$^{-1}$; chemical ionization mass spectra M+H=276, $C_{13}H_{10}FN_3O_3$ requires M+H= 276.

8-Fluoro-5,6-dihydro-5-methyl-6-oxo-4H-imidazo[1,5-a] [1,4]benzodiazepine-3-carboxylic Acid, 2-[[(1,1-dimethylethoxy)carbonyl] amino]propyl Ester (2)

To a stirred solution of (1) (0.30 g, 1.09 mmol), 4-(N,N-dimethylamino)pyridine (0.13 g, 1.09 mmol) and 3-(N-t-butyloxycarbonyl) aminopropanol (0.38 g, 2.17 mmol) in dry methylene chloride (5 ml) was added N,N'-dicyclohexylcarbodiimide (0.44 g, 2.17 mmol), and the solution was stirred overnight at room temperature. The precipitated N,N'-dicyclohexylurea was filtered off and washed with 10 ml of ether. The combined filtrate and washings were evaporated in vacuo, and the resulting residue was fractionated by column chromatography on silica gel, eluting with concentrated aqueous ammonia/methanol/chloroform (1:9:90). Fractions corresponding to the major product were evaporated in vacuo to give 2 (0.19 g, 40%) as a colorless oil: $^1$H NMR (CDCl$_3$) 1.44 (s, 9H, t-Bu), 2.02 (t, J=6.3 Hz, 2H), 3.25 (s, 3H, NMe), 3.29 (m, 2H), 3.66 (t, 2H, J=5.7 Hz), 4.40 (m, 1H), 4.44 (t, 2H, J=6.1 Hz), 4.60–5.00 (m, 1H, NH), 5.22 (m, 1H), 7.32–7.45 (m, 2H), 7.78 (dd, 1H, J=2.8 Hz, J=8.7 Hz), 7.86 (s, 1H); high resolution mass measurements m/z calculated for C$_{21}$H$_{25}$N$_4$O$_5$F 432.1807, m/z found 432.1796.

8-Fluoro-5,6-dihydro-5-methyl-6-oxo-4H-imidazo[1,5a][1,4]benzodiazepine-3-carboxylic Acid, 3-Aminopropyl Ester (3)

To a stirred solution of 2 (0.19 g, 0.44 mmol) in dry chloroform (5 ml) at 0° C. was added trifluoroacetic acid (1.0 ml), and stirring was continued for 1 h at 0° C. The solvent was evaporated in vacuo, and the oily residue was subjected to high vacuum to give 3 trifluoroacetate (quantitative) as a colorless oil. No attempt was made to store this compound as the free base because of its inherent lability for rearrangement. However, for the purposes of characterization, a small portion of the salt was converted to the free base by partitioning between chloroform and saturated NaHCO$_3$. 3 free base exhibited: $^1$H NMR (CDCl$_3$) δ 1.97 (m, 4H), 2.91 (m, 2H), 3.25 (s, $^3$H), 4.41 (m, 1H), 4.48 (br s, 2H, NH$_2$), 5.20 (m, 1H), 7.32–7.47 (m, 2H), 7.78 (dd, 1H, J=2.8 Hz, J=8.7 Hz), 7.89 (s, 1H); IR (CHCl$_3$) 3680, 3400, 3010, 1705, 1645, 1585, 1500, 1280, 1230, 1180, 1060 cm$^{-1}$; high resolution mass measurements m/z calculated for C$_{16}$H$_{17}$FN$_4$O$_3$ 332.1277, m/z found 332.1284.

8-Fluoro-5,6-dihydro-5-methyl-6-oxo-4H-imidazo[1,5a]01,4]benzodiazepine-3-carboxylic Acid, 3-[(7-Nitro-4-benzofurazanyl)] -amino]propyl Ester (BD 623)

To a stirred mixture of 4-fluoro-7-nitrobenz-2-oxa- 1,3-diazole (9.5 mg, 0.0516 mmol) and 3 (57 mg, 0.128 mmol) in dry dimethylformamide (2.0 ml) was added triethylamine (100 µl, 0.719 mmol) and the reaction was stirred for 18 h at room temperature. The dimethylformamide was evaporated under high vacuum at 60° C. The residue was taken up in 1 ml of methanol and applied to one silica gel plate (1 mm×20 cm×20 cm) (Analtech GF) eluting with concentrated aqueous ammonia/methanol/chloroform (1:9:90). The major fluorescent band was removed from the plate and extracted by stirring with 30 ml of the same solvent system. Filtration of the silica gel and evaporation of the solvent afforded 22.6 mg (88% based on starting amount of NBD fluoride) of BD-623 as an amorphous solid. $^1$H NMR (d$_6$.Me$_2$SO) δ 1.10–1.27 (m, 2H), 2.18 (t, 2H, J=6.2 Hz), 3.34 (s, 3H NMe), 3.66 (m, 2H), 4.49 (m, 2H), 4.42 (m, 1H), 5.00 (m, 1H), 6.48 (d, 1H, J=9.0 Hz), 7.69 (d, 1H, J=8.3 Hz), 7.82 (m, 1H), 8.35 (s, 1H), 8.50 (d, 1H, J=9.0 Hz), Cf-252 MS m/z 496 (MH$^+$), 5.18 (MNa$^+$), 540 (MNa$_2^{2+}$-H$^+$). BD 623 was stored at −20° C. in the dark until ready for use. Solutions of BD 623 in Me$_2$SO did not undergo detectable decomposition (assessed by TLC) for several months when stored in the dark at −80° C.

Absorption spectra were measured with a Gilford Response spectrophotometer using 1-cm quartz cuvettes. The adsorption maxima were coincident with the excitation maxima (within experimental error) determined by fluorescence. Fluorescence excitation and emission spectra (uncorrected) were measured with a Spex Flurolog 1680 fluorimeter with DM-3000 software (Spec Industries, Edison, N.J.). Real time and wavelength spectral measurements were made with the fluorimeter operating in a ratio mode. Measurements were carried out in 1-cm acrylic cuvettes (W. Sarstedt, Newton, N.C.) with the samples maintained at ambient temperature (22°–23° C.). The quantum yield of BD 623 was determined using an aqueous sodium fluorescein solution as a standard. The total emitted energy (excitation wavelength, 486 nm) of BD 623 (the integrated area under the emission spectrum) was compared to sodium fluorescein under identical conditions where the quantum yield of the standard was 0.92 (18).

The excitation and emission maxima of BD 623 are 486± 2 and 542±2 nm, respectively. The extinction coefficient (e) of BD 623 (22° C.) in 50 mM Tris citrate (pH 7.4) buffer is 17,600 M$^{-1}$ cm$^{-1}$, with a quantum yield of 0.02 using sodium fluorescein as a standard.

EXAMPLE 4

Binding studies with BD-623

Tissues were prepared as described in example 2. In experiments using Ro 15-4513 as a photoaffinity label, membranes were resuspended in 30 volumes of 50 mM Tris buffered to pH 7.4 with sodium-free citric acid following the initial centrifugation step. The membranes were incubated at 4° C. for 15 min in plastic Petri dishes exposed to 366 nm UV irradiation in the presence of 50 nM Ro 15-4513, described by Sieghart, W., et al., *J. Neurochem.* 48, 46–52 (1985). The tissues were centrifuged at 20,000×g for 20 min, and the pellets were washed four additional times in 50 volumes of Tris citrate buffer. The final pellet was suspended in 10 or 40 volumes of the same buffer for fluorescence and radioligand binding assays, respectively. Control membranes were either irradiated in the absence of Ro 15- 4513 or incubated with Ro 15-4513 and extensively washed without exposure to UV.

RADIOLIGAND BINDING ASSAYS

[$^3$H] Ro 15-1788 binding was assayed (22° C.) in a volume of 0.5 ml consisting of 50 µl of [$^3$H] Ro 15-1788 solution, 50 µl of tissue suspension, 300 µl of 50 mM Tris citrate buffer, and drugs or buffer to volume. The reaction was initiated by the addition of tissue and terminated after 60 min by filtration over GF/B filters and washing with two 5-ml aliquots of Tris citrate buffer using a Brandel M-48R filtering manifold (Brandel Instruments, Gaithersburg, Md.). Nonspecific binding was determined in the presence of 100 µM flurazepam. K$_d$ and B$_{max}$ estimates were performed with 0.5–32 nM concentrations of radioligands. The K$_I$ of BD 623 was estimated using 2–64 nM concentrations of fluorescent ligand and 1.0 nM radioligand. The radioactivity retained by the filters was measured in a Beckman LS 5801 liquid scintillation counter.

FLUORESCENCE ASSAYS

Tissue suspensions (2 ml) were incubated in 1-cm acrylic cuvettes (22°–23° C.) with constant stirring. Stock solutions of BD 623 and drugs were diluted in buffer and added (in 10 µl aliquots) sequentially as indicated to yield the desired final concentrations. The final concentration of Me$_2$SO in the assay was ≦0.006%. This concentration of Me$_2$SO has no detectable effect on ligand binding to benzodiazepine receptors. The sample was excited at 486 nm, and emission was monitored at 542 nm with narrow band-pass slits and cross polarizers to minimize light scattering.

PROTEIN DETERMINATION

Protein content was determined using the method of Miller, G. *Anal. Chem.* 31, 964–971 (1959) with bovine serum albumin as a standard.

Figure 2A:
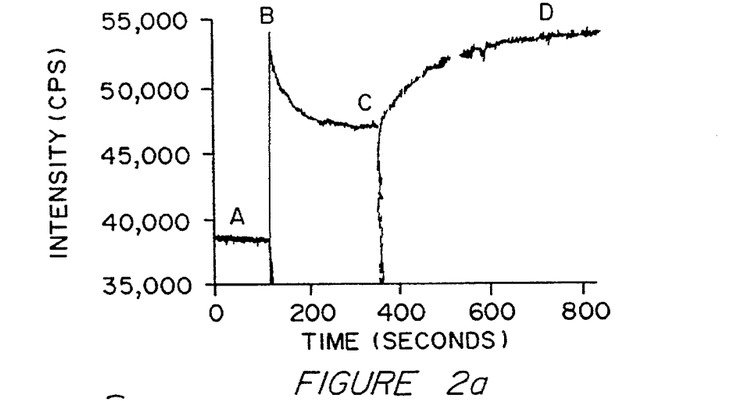
FIGS. 2A, 2B, and 2C, are the fluorescent characteristics of BD 623 in brain membranes. A, time-based fluorescence scan. Region A, tissue only (autofluorescence); BD 623 (12.5 nM) and flurazepam (100 μM) were added to the cuvette at points B and C, respectively. Region D is the dequenching plateau. The addition of drugs had only a negligible effect on fluorescence intensity since the resultant dilution was ≤1% of the total volume. B, BD-623 fluorescence as a function of concentration in 50 mM Tris citrate buffer (circles) and in tissue (0.158 mg/100 μl; 3.16 mg/assay) containing 100 μM flurazepam (squares). C, relationship between protein concentration and fractional quenching of BD-623 (12.5 nM) fluorescence. Relative protein concentration of 1 is 3.12 mg/assay. The correlation coefficient for this line was 0.996.

The fluorescent behavior of BD-623 in the presence of benzodiazepine receptors was examined by exciting tissue and ligand with monochromatic light (486 nm) and monitoring emission intensity (542 nm) at 1-s intervals. After determining background tissue fluorescence (autofluorescence) (FIG. 2A, segment A), BD-623 was added to the stirred membrane suspension (FIG. 2A, point B). A time-dependent quenching of fluorescence was observed until a plateau was reached (FIG. 2A, interval BC). At point C (FIG. 2A), an excess of flurazepam (final concentration 100 μM) was added, and fluorescence dequenching was monitored until a plateau was reached (FIG. 2A, region D). This concentration of flurazepam produced a negligible amount of fluorescence at 542 nm (<0.1% of the total fluorescence intensity). A similar dequenching was observed when a large excess ($\geq$μM) of other high affinity benzodiazepine receptor ligands (diazepam, CGS 8216, Ro 15-1788, and clonazepam) were added instead of flurazepam at point C. These substances did not contribute significantly to the total fluorescence at the concentrations employed. Non-benzodiazepine receptor ligands such as buspirone, naloxone, and phenteramine (10 μM) did not effect a dequenching of fluorescence. The difference in fluorescence intensity between D and C (D-C) represents the amount of fluorescence that can be specifically dequenched by an excess of benzodiazepine receptor ligands but not other compounds and is referred to as "specific quenching." When specific quenching is expressed as a fraction of the total fluorescence attributable to BD 623 (D-A, FIG. 2A), this ratio ([D-C]/[D-A]) is referred to as "fractional quenching."

Figure 2B:
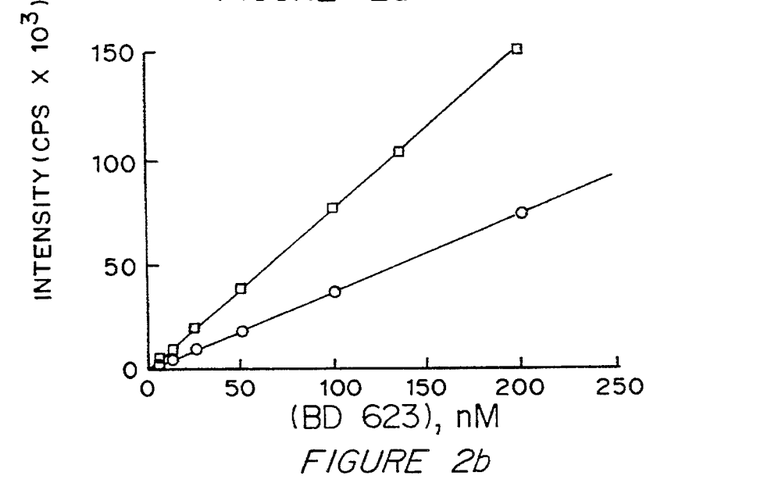

Since the quantum yield of the fluorophore NBD has been reported to be dependent upon the polarity of its environment, the fluorescence intensity of BD-623 was measured in buffer and in the presence of tissue containing 100 μM flurazepam. Fluorescence in Tris citrate buffer increased linearly as a function of ligand concentration in the presence or absence of tissue (FIG. 2B). However, fluorescence intensity was significantly greater in the presence (FIG. 2B, squares) than in the absence (FIG. 2B, circles) of tissue. An increased quantum yield of BD-623 was also observed in heat-denatured membranes (boiling water bath for 10 min) as well as in 10% and 20% ethanol.

Figure 2C:
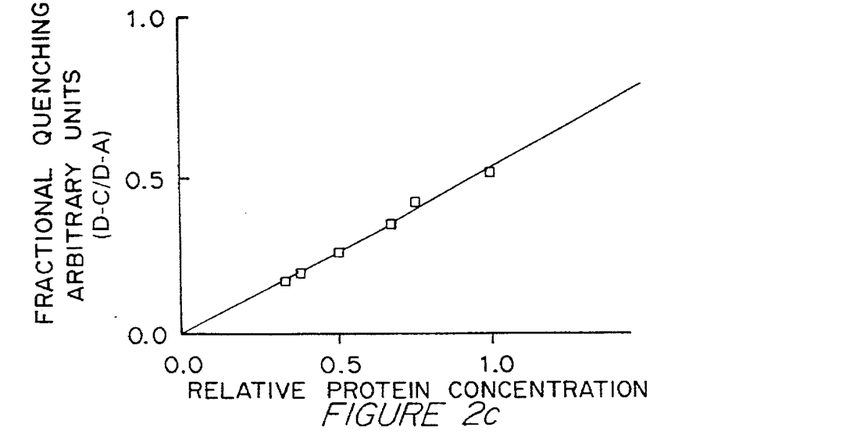

The specific quenching of BD-6223 (12.5 nM) was linear with protein concentration (FIG. 2C) and dependent upon the presence of unoccupied benzodiazepine receptors. Tissues were photoaffinity-labeled with Ro 15-513 (50 nM) followed by extensive washing. This procedure reduced the maximum number of binding sites ($B_{max}$) estimated using [$^3$H] Ro 15-1788 by 83%. In an aliquot of these photoaffinity-labeled membranes, the quenched fluorescence of BD-623 was reduced by 77%.

The effect of ligand concentration on fluorescence quenching was determined by construction of saturation isotherm with BD 623, representing a fluorescence quenching/dequenching tracing at BD 623 concentrations ranging from 6.25–100 nM. Tissue autofluorescence was subtracted. Preparations were dequenched with flurazepam (100 μM).

The $K_d$ and $B_{max}$ obtained in arbitrary fluorescence units were converted to molarity using linear regression between fluorescence intensity and BD 623 concentration. In constructing saturation isotherms for BD-623, it was assumed that the fluorescence intensity of the bound ligand is negligible compared to the free form. This assumption is supported by the finding that the fractional quenching [(D-C)/(D-A)] of BD 623 fluorescence is equal to the expected (theoretical) fractional binding of BD-623 (bound, B is calculated from the equation.

Specific quenching at each concentration was plotted versus unquenched fluorescence. $B_{max}$ and $K_d$ were estimated from this curve (in arbitrary fluorescence units) with the resulting values converted to conventional molarity units using a standard curve. These methods yielded $K_d$ and $B_{max}$ values of 13.9±0.2 nM and 7.2±0.4 pmol/mg of protein (n=3), respectively. The $K_i$ of BD 623 estimated by competition experiments using [$^3$H] Ro 15-1788 was 5.7±0.3 nM (n=3), and the $B_{max}$ estimated with this radioligand was 2.3±0.2 pmol/mg of protein.

The apparent affinity of Ro 15-1788 for benzodiazepine receptors was estimated by fluorescence quenching of BD-623. Membranes were preincubated with Ro 15-1788 (0–80 nM) prior to addition of BD-623, and the quenching/dequenching of the fluorescent ligand was monitored. Plotting the fractional quenching of BD-623 fluorescence from each curve versus the log concentration of Ro 15-1788 results in a conventional competition curve with an $IC_{50}$ of 26.4 nM ($K_i$ 8.0 nM) and pseudo-Hill coefficient of 1.2. The apparent $K_d$ of [$^3$H] Ro 15-1788 was 1.8± 0.1 nM (n=3) estimated using the filtration technique described above.

The fluorescence quenching assay of BD 623 binding to control (nonirradiated) tissue was determined. Exposure to 366 nm UV light without Ro 15-1788 resulted in curves that were virtually superimposable with control tissue. The specific quenching of BD 623 was reduced by 77% in photoaffinity-labeled membranes. The concentration of BD 623 was 100 nM, and dequenching was achieved with flurazepam (100 μM). The values (B) were obtained by constructing saturation isotherms for [$^3$H] Ro 15-1788. Photoaffinity labeling reduced the $B_{max}$ of [$^3$H] Ro 15-1788 by 83%. $K_d$ values for [$^3$H] Ro 15-1788 in this representative experiment were: 1.4 nM (photoaffinity-labeled), 2.1 nM (UV-treated only), and 1.3 nM (Ro 15-513 exposed and extensively washed). The respective $B_{max}$ values were 260, 1500, and 1470 fmol/mg of protein. Nonspecific binding was defined with 100 μM flurazepam.

Inhibition of BD 623 specific fluorescence by Ro 15-1788 was based on an estimation of the potency of a competing benzodiazepine receptor ligand. Membranes were incubated for 15 min with Ro 15-1788 (0–80 nM) prior to the addition of BD 623 (50 nM). Dequenching was achieved with 100 μM flurazepam. Fractional BD 623 quenching as a function of Ro 15-1788 concentration was determined. The $IC_{50}$ of Ro 15-1788 was 26.4 nM, and a pseudo-Hill coefficient of -1.2 was obtained. The $K_i$ of Ro 15-1788 was 8.02 nM calculated as described by Munson, P., and Rodbard, D., *J. Recept. Res.* 8, 547–559 (1988).

Since the attachment of an NBD moiety to Ro 15-1788 resulted in only a modest diminution in the apparent affinity of BD-623 ($K_i$ 5.7 nM) for benzodiazepine receptors compared to the parent molecule ($K_d$ 2.8 nM), the feasibility of quantitating the binding of this high affinity ligand to benzodiazepine receptors was examined by monitoring fluorescence in real time. After determining fluorescence of the membrane preparation (autofluorescence), BD-623 was added and fluorescence was monitored over time. Fluorescence was gradually quenched to a plateau when addition of excess flurazepam effected a dequenching of fluorescence that was monitored to equilibrium. While a similar dequenching was effected by other benzodiazepine receptor ligands (CGS 8216, Ro 15-1788, lorazepam, and diazepam), it was not observed in the presence of substances that do not bind to benzodiazepine receptors. Moreover, fluorescence quenching was prevented if the membranes were preincubated with a large molar excess of benzodiazepine receptor ligands prior to addition of BD-623.

Modifications and variations of the method and compositions of the present invention will be obvious to those skilled in the art from the foregoing detailed description of the invention. Such modifications and variations are intended to come within the scope of the following claims.

We claim:

1. A fluorescently labelled conjugate comprising ligand, and a fluorescent label bound to the ligand to form a fluorescently labelled conjugate wherein the label, when bound to the ligand, does not hinder binding of the ligand to a benzodiazepine receptor, wherein the fluorescently labeled conjugate binds specifically to the receptor with an affinity of less than or equal to one micromolar and the label is directly detectable in the visible spectrum.

2. The conjugate of claim 1 wherein the affinity of the labeled conjugate is less than or equal to 100 nanomolar.

3. The conjugate of claim 1 wherein the label is selected from the group consisting of fluorescein, fluorescent derivatives of fluorescein, Texas red, nitrobenz-2-oxa-1,3-diazol-4-yl (NBD), coumarin, dansyl chloride, rhodamine and fluorescent derivatives of rhodamine.

4. The conjugate of claim 1 wherein the conjugate is BD 623.

5. The conjugate of claim 1 wherein the conjugate is BD 621.

6. The conjugate of claim 1 wherein the ligand and the label are linked by a spacer.

* * * * *